United States Patent
Bielawski et al.

(10) Patent No.: US 8,287,737 B2
(45) Date of Patent: Oct. 16, 2012

(54) SEALING ASSEMBLY FOR A CHROMATOGRAPHY COLUMN

(75) Inventors: Jacek Bielawski, Uppsala (SE); Erik Hammarstrand, Uppsala (SE); Tomas Agren, Uppsala (SE)

(73) Assignee: GE Healthcare Bio-Sciences AB, Uppsala (SE)

(*) Notice: Subject to any disclaimer, the term of this patent is extended or adjusted under 35 U.S.C. 154(b) by 352 days.

(21) Appl. No.: 12/676,395

(22) PCT Filed: Sep. 26, 2008

(86) PCT No.: PCT/SE2008/000532
§ 371 (c)(1),
(2), (4) Date: Mar. 4, 2010

(87) PCT Pub. No.: WO2009/041877
PCT Pub. Date: Apr. 2, 2009

(65) Prior Publication Data
US 2010/0230340 A1    Sep. 16, 2010

(30) Foreign Application Priority Data

Sep. 28, 2007 (GB) .................................. 0718993.9

(51) Int. Cl.
*B01D 15/08* (2006.01)
(52) U.S. Cl. .................................. 210/656; 210/198.2
(58) Field of Classification Search .................. 210/635, 210/656, 659, 198.2, 238, 282; 96/101, 105, 96/106
See application file for complete search history.

(56) References Cited

U.S. PATENT DOCUMENTS

| | | | | |
|---|---|---|---|---|
| 2,814,540 A | * | 11/1957 | Southerwick | 92/194 |
| 4,889,351 A | | 12/1989 | Frost | |
| 4,891,133 A | * | 1/1990 | Colvin, Jr. | 210/198.2 |
| 5,169,522 A | * | 12/1992 | Shalon et al. | 210/198.2 |
| 5,378,361 A | * | 1/1995 | Baeckstrum | 210/198.2 |
| 5,423,982 A | * | 6/1995 | Jungbauer et al. | 210/198.2 |
| 5,671,928 A | | 9/1997 | Lanyi et al. | |
| 6,802,968 B2 | * | 10/2004 | Leavesley et al. | 210/198.2 |
| 6,932,904 B2 | * | 8/2005 | Laub et al. | 210/198.2 |
| 7,258,060 B2 | * | 8/2007 | Dahl | 92/194 |
| 2006/0049090 A1 | * | 3/2006 | Spoldi et al. | 210/198.2 |
| 2006/0066058 A1 | | 3/2006 | Holt et al. | |
| 2006/0156918 A1 | * | 7/2006 | Dahl | 92/240 |

FOREIGN PATENT DOCUMENTS

| | | |
|---|---|---|
| CN | 2195660 Y | 4/1995 |
| GB | 2 177 464 | 1/1987 |
| GB | 2 308 635 | 7/1997 |
| WO | WO2004/059314 | 7/2004 |

OTHER PUBLICATIONS

First Office Action on Copending Chinese Application No. 200880109670.X Dated Mar. 30, 2012.

* cited by examiner

Primary Examiner — Ernest G Therkorn

(57) ABSTRACT

The present invention relates to a sealing assembly for use in chromatography columns and methods for forming a seal in such columns. The assembly comprises a sealing element composed of a material having a low coefficient of friction and a separate resilient member co-operating therewith. The seal provided is stable over a temperature range of +2° C. to +30° C.

13 Claims, 5 Drawing Sheets

SEALING ASSEMBLY FOR A CHROMATOGRAPHY COLUMN

CROSS-REFERENCE TO RELATED APPLICATIONS

This application is a filing under 35 U.S.C. §371 and claims priority to international patent application number PCT/SE2008/000532 filed Sep. 26, 2008, published on Apr. 2, 2009, as WO 2009/041877, which claims priority to patent application number 0718993.9 filed in Great Britain on Sep. 28, 2007.

FIELD OF THE INVENTION

The present invention relates to a seal for a chromatography column. In particular, the invention provides improved sealing between the adapter and the internal walls of the column when the adapter is static or in motion. The invention also allows removal of particulate media from sides of the column walls.

BACKGROUND OF THE INVENTION

Chromatography columns provide a means for separating, purifying and isolating chemical and biological compounds. The size and type of column used in these operations typically depends upon the scale of the process in question, small glass or plastic walled columns typically being used for research purposes, while larger metal columns are employed for industrial processes. For instance, chromatography columns may be used in manufacturing processes to purify process liquids and separate substances of interest from such liquids; typical examples include large-scale preparative purification of fine chemicals and pharmaceuticals, together with biological products.

Whilst the present invention relates to both glass/plastic walled and larger metal walled chromatography columns, it is particularly useful for manufacturing and industrial-scale chromatography columns.

Industrial-scale chromatography columns typically comprise a hollow, axially vertical tubular housing including a liquid inlet at the upper end and through which the buffer and substances to be separated are dispensed to the media bed located within the cavity of the tube, and a liquid collecting system at the lower end for collecting substances and buffer. The particulate chromatographic media or bed through which the buffer fluid and/or substances to be separated and purified percolates is located between the liquid inlet and collecting system.

An adapter assembly is typically affixed to the upper end of the tubular housing and a base assembly to the lower end where it is bolted to the bottom flanges. Each of these assemblies typically comprises a strong backing plate and a distributor plate which further supports a bed support; a bed support is a layer of mesh, screen, filter, sinter or other fluid-permeable media-retaining material which permits process liquid flow into and out of the chromatography bed space or cavity while retaining the bed of particulate medium. To provide adjustability and control of the bed height and bed compression, the adapter assembly is typically made in the form of a piston or sliding adapter in the column tube interior. After the column is charged with bed media, typically through a valve or nozzle, the adapter may be forced toward the bottom of the tube to compress or pressurize the media bed. Generally the base assembly is a fixed structure which is bolted against the bottom flange of the column tube but, in some instances, may also be in the form of a movably slidable piston or adapter.

The backing plate of the base assembly generally acts as a support for the column, being itself supported on legs or some other stand arrangement which allows clearance for outlet pipework projecting beneath the base assembly.

A problem often encountered in the use of both laboratory and industrial-scale chromatography columns is the leakage of liquid, such as buffer or mobile phase, or particulate media material, from the bed space or cavity past the adapter or piston. Seals, such as O-rings, are commonly used to prevent such leakage but these tend to perform poorly under operating conditions due to abrasion and inadequate sealing. The resulting leakage can lead to poor chromatographic performance due to liquid losses and also to bacterial contamination where liquid collects in dead spaces between the O-ring and the adapter wall.

U.S. Pat. No. 5,671,928 describes a seal for small, glass or plastic walled columns which is claimed to provide good releasability and sealing capabilities, allows visual inspection that a seal has been made, increased chromatographic efficiency and a substantial reduction in bacterial growth. However, the seals disclosed in U.S. Pat. No. 5,671,928 are made from a resilient seal material such as rubber that require a coating with a friction-reducing polymer such as polytetrafluoroethylene to reduce abrasion. Such coatings are difficult to apply and tend not to be permanent in nature. Furthermore, the seals described in this document are self-compensating to the extent that an increase in pressure increases the sealing force. Such a design can cause problems due to the resulting increased friction and abrasion.

There is thus a need to provide improved seals for use in chromatography columns in order to maintain high levels of chromatographic performance under normal packing and operating pressures. Preferably the seals should be flexible enough for use in a range of columns to obviate the need for high levels of tolerance in manufacturing the internal column walls. In addition to preventing leakage of buffer or liquid from the bed space past the adapter or piston, thereby reducing microbiological contamination, such seals should preferably be capable of cleaning, removing and compressing particulate media from the internal walls of the column to aid the packing process and further reduce the risk of leakage. Furthermore, the seals should be stable across the temperature ranges under which the chromatographic column is required to operate.

SUMMARY OF THE INVENTION

In a first aspect of the present invention, there is provided a method for forming a seal within a chromatography column between an adapter and an inner cylindrical surface of a cylindrical housing by means of a sealing assembly positioned therebetween, the assembly comprising a sealing element composed of a material having a low coefficient of friction and a separate resilient member for co-operating therewith, the sealing element comprising opposed first and second faces, wherein the first face comprises a sealing surface and the second face comprises a compressive surface, wherein the resilient member exerts a force against the compressive surface of the sealing element to form a seal between the sealing surface and the cylindrical surface.

Preferably, the sealing element is composed of a material which has a coefficient of friction in the range of 0.5 to 2.0. Materials such as certain forms of ABS (Acrylonitrile Butadiene Sytrene) and rubber have values in this range. More preferably, the material of the sealing element has a coefficient of friction in the range of 0.2 to 0.5. Many plastic materials such as certain forms of ABS, PEEK (Polyetheretherketone), PA (Polyamide) and PC (Polycarbonate) have values in this range. Most preferably, the sealing element is composed of a material having a coefficient of friction in the range of 0.001 to 0.2. UHMWPE (UltraHigh Molecular Weight Polyethylene) has a coefficient of friction in the range of 0.13 to 0.2 (see website for Lehigh Valley Plastics) whilst PTFE (polytetrafluoroethylene) has a coefficient of friction in the range of 0.05 to 0.13 (see websites for Dotmar and Toray Fluorofibers).

Preferably, the sealing element comprises a first and a second leg, the first leg comprising opposed first and second faces, the first face being a sealing surface comprising a raised leading and a raised trailing edge, the second face comprising a compressive surface, and the second leg comprising a compressive surface; wherein the resilient member exerts a force against said compressive surfaces of the sealing element to form a seal between said raised leading and trailing edges and said cylindrical surface. This configuration achieves a superior seal compared to conventional seals in the art and also provides improved media cleaning properties.

Preferably, the assembly is movable along the axial axis of the cylindrical surface and thus forms a dynamic seal.

Suitably, the sealing element is L-shaped. Other shapes, such as U-shapes, are also possible.

Suitably, the compressive surfaces of the first and second legs of the sealing element are indented at their intersection to maximise and/or concentrate the force exerted on the raised leading and trailing edges on the cylindrical surface. This improves the strength of the seal obtained between the edges and the surface.

Preferably, the compressive surfaces of the first and second legs of the sealing element are angled relative to said indent to maximise and/or concentrate the force exerted by the resilient member on the raised leading and trailing edges on the cylindrical surface. This improves the strength of the seal obtained between the edges and the surface.

Preferably, the sealing element is composed of ultra high molecular weight polyethylene (UHMWPE).

Preferably, the resilient member is an O-ring. More preferably, the resilient member is an O-ring composed of a fluoroelastomer or an EPDM rubber.

Suitably, the strength of the seal formed between the sealing surface and the cylindrical surface is independent of the pressure applied to the adapter.

Preferably, the seal is stable across a temperature range of +2° C. to +36° C. More preferably, the seal is stable across the temperature range of +4° C. to +30° C.

Preferably, the seal is stable across a pressure range of −0.8 bar to +20.0 bar. More preferably, the seal is stable across the pressure range of −0.5 bar to +5.7 bar.

According to a second aspect of the present invention, there is provided a sealing assembly for a chromatography column for sealing between an adapter and an inner cylindrical surface of a cylindrical housing,
the assembly comprising a sealing element composed of a material having a low coefficient of friction and a separate resilient member co-operating therewith,
the sealing element comprising a first and a second leg wherein,
the first leg comprises opposed first and second faces, the first face being a sealing surface comprising a raised leading and a raised trailing edge, the second face comprising a compressive surface, and the second leg comprising a compressive surface;
wherein the resilient member exerts a force against the compressive surfaces of the sealing element to form a seal between the raised leading and trailing edges and the cylindrical surface.

Preferably, the sealing element is composed of a material which has a coefficient of friction in the range of 0.5 to 2.0. Materials such as certain forms of ABS (Acrylonitrile Butadiene Sytrene) and rubber have values in this range. More preferably, the material of the sealing element has a coefficient of friction in the range of 0.2 to 0.5. Many plastic materials such as certain forms of ABS, PEEK (Polyetheretherketone), PA (Polyamide) and PC (Polycarbonate) have values in this range. Most preferably, the sealing element is composed of a material having a coefficient of friction in the range of 0.001 to 0.2. UHMWPE (UltraHigh Molecular Weight Polyethylene) has a coefficient of friction in the range of 0.13 to 0.2 (see website for Lehigh Valley Plastics) whilst PTFE (polytetrafluoroethylene) has a coefficient of friction in the range of 0.05 to 0.13 (see websites for Dotmar and Toray Fluorofibers).

Preferably, the assembly is movable along the axial axis of the cylindrical surface and thus forms a dynamic seal.

Preferably, the sealing element is L-shaped. Other shapes, such as U-shapes, are also possible.

Preferably, the compressive surfaces of the first and second legs of the sealing element are indented at their intersection to maximise and/or concentrate the force exerted on the raised leading and trailing edges on the cylindrical surface. This improves the strength of the seal obtained between the edges and the surface.

Preferably, the compressive surfaces of the first and second legs of the sealing element are angled relative to the indent to maximise and/or concentrate the force exerted by the resilient member on the raised leading and trailing edges on the cylindrical surface. This improves the strength of the seal obtained between the edges and the surface.

Preferably, the sealing element is composed of ultra high molecular weight polyethylene (UHMWPE).

Preferably, the resilient member is an O-ring. More preferably the resilient member is an O-ring composed of a fluoroelastomer or an EPDM rubber.

Preferably, the strength of the seal formed between the raised leading and trailing edges and the cylindrical surface is independent of the pressure applied to the adapter.

Preferably, the seal so formed is stable across a temperature range of +2° C. to +36° C. More preferably, the seal is stable across the temperature range of +4° C. to +30° C.

Preferably, the seal is stable across a pressure range of −0.8 bar to +20.0 bar. More preferably, the seal is stable across the pressure range of −0.5 bar to +5.7 bar.

According to a third aspect of the present invention, there is provided a chromatography column comprising a cylindrical housing having an inner cylindrical surface, an adapter within the housing, and a sealing assembly for forming a seal between the adapter and the inner cylindrical surface, the assembly comprising a sealing element composed of a material having a low coefficient of friction and a resilient member co-operating therewith,
the sealing element comprising opposed first and second faces, wherein the first face comprises a sealing surface and the second face comprises a compressive surface,
wherein the resilient member exerts a force against the compressive surface of the sealing element to form a seal between the sealing surface and the cylindrical surface.

Preferably, the column comprises the sealing assembly as hereinbefore described.

In a fourth aspect of the invention, there is provided a method of sanitising a chromatography column, the method comprising treating the column comprising the sealing assembly as hereinbefore described with a sanitising agent and then neutralising the agent. Examples of suitable sanitising agents include acids, bases and antimicrobial chemicals. Bases, such as sodium hydroxide, at appropriate concentrations (e.g. 1 M) are particularly suitable as sanitising agents. Suitable neutralising agents include water, acids and bases.

Dynamic seals as described herein should be useful in a wide variety of applications involving both multi-use (e.g. fixed) devices and disposable devices as well as connections between two such devices. Possible uses include chromatography, centrifugation, filtration, sedimentation, electrophoresis and other preparative and analytical scale devices for processing not just macromolecules and other nanometer scale colloids but also micrometer scale colloids such a bacterial cells, virus particles, and eukaryotic cells in applications related, for example, to waste treatment, biopharmaceutical production, cell banking, cell therapy and research.

It will be understood that other variants of the sealing assembly of the invention are possible including those having different shapes which allow cooperation of the O-ring with the sealing element. One such example is a U-shaped sealing element having three legs into which the O-ring can be inserted and the entire assembly fitted in an appropriate gland or recess adjacent the adapter and cylindrical column wall; in this configuration, the O-ring will compress at least two of the legs of the sealing element to lock it into position within the recess and force the sealing surface of the element against the column wall to form a seal therebetween.

BRIEF DESCRIPTION OF THE DRAWINGS

The invention is further illustrated by reference to the following figures in which.

DETAILED DESCRIPTION OF THE INVENTION

Figure 1:
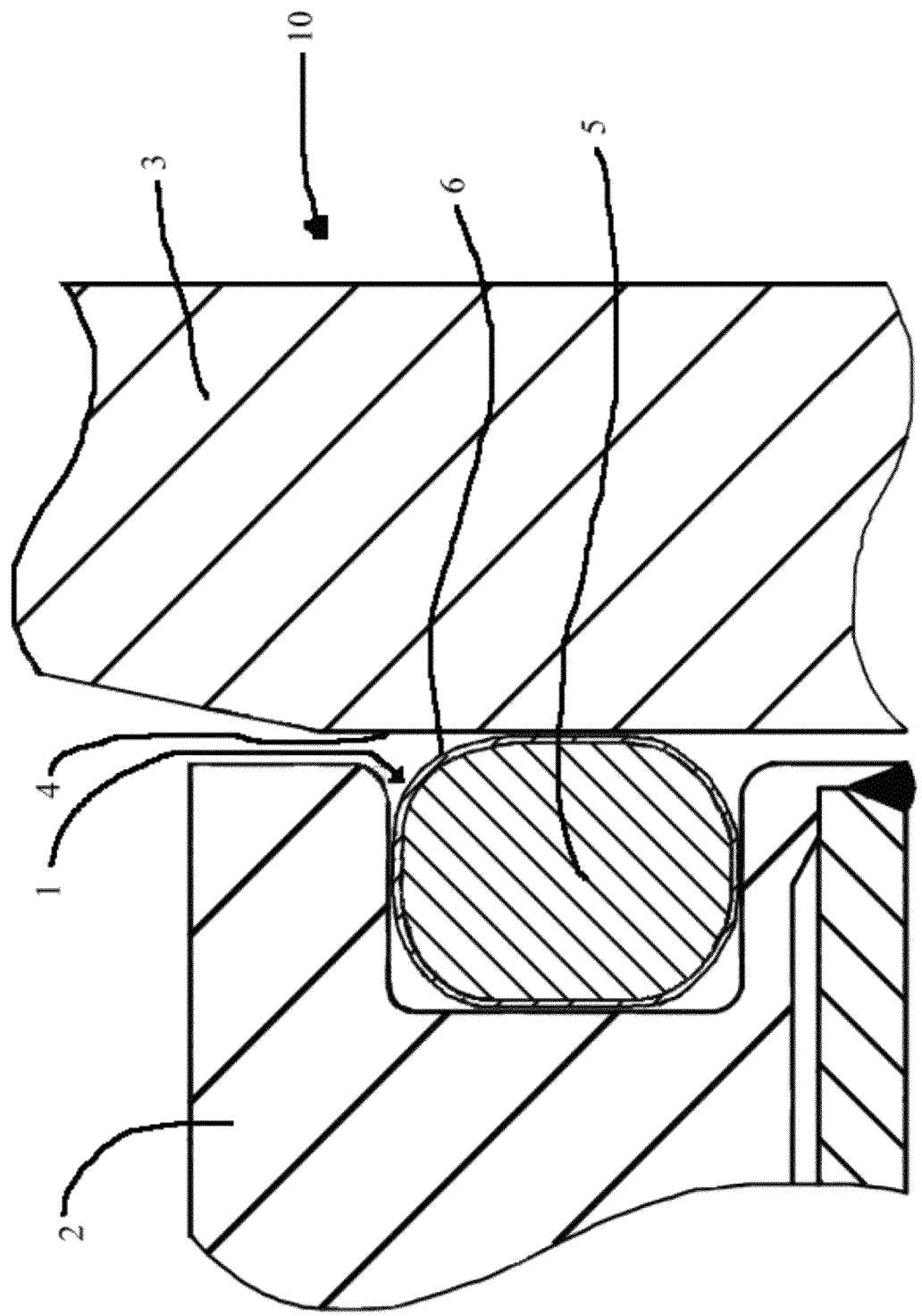
FIG. 1 is a cross-sectional view of an adapter adjacent to the interior wall of a chromatography column showing an O-ring used in the prior art to reduce leakage within the column.

O-rings are commonly used as seals within chromatography columns. In the cross sectional view of FIG. 1, an O-ring 1 is shown forming a seal between an adapter 2 and a cylindrical wall 3 having an internal surface 4 of a chromatography column 10. The core 5 of the O-ring is composed of silicone but may be made of other suitable resilient elastomeric materials such as VITON® (see website for Dupont Elastomers), and is encapsulated with a coating 6 of a suitable friction-reducing polymer such as TEFLON® FEP (see website for Dupont). The wall 3 of the column 10 may be made of glass, plastic or a suitable metal such as stainless steel.

Tests with O-rings 1 having a silicone core 5 encapsulated in a TEFLON® FEP coating 6 showed high levels of pressure drop under standard column operating conditions, pressure drops of up to 15% being observed over a 2 hour period in some instances. In comparison, the sealing assembly of the present invention formed a far tighter seal with pressure drops in the range of 0.25 to 1% being observed under the same operating conditions and time period.

The significant pressure drops observed with the TEFLON® FEP encapsulated O-ring may be due to the abrasive nature of the fluorinated ethylene propylene resin which wears down readily, leading to an accumulation of FEP within the column. The polymer may also abrade the plastic/acrylic column wall, causing scratching and reducing its sealing properties.

Furthermore, the seal obtained with TEFLON® FEP encapsulated O-rings varied with temperature, possibly due to the seal being sensitive to compression set in that it tries to shape itself to its environment. Moreover, the shape of O-rings was found to be unsuitable for removing media particles from the column wall which may themselves prove abrasive to the surface of the wall.

Figures 2A, 2B:
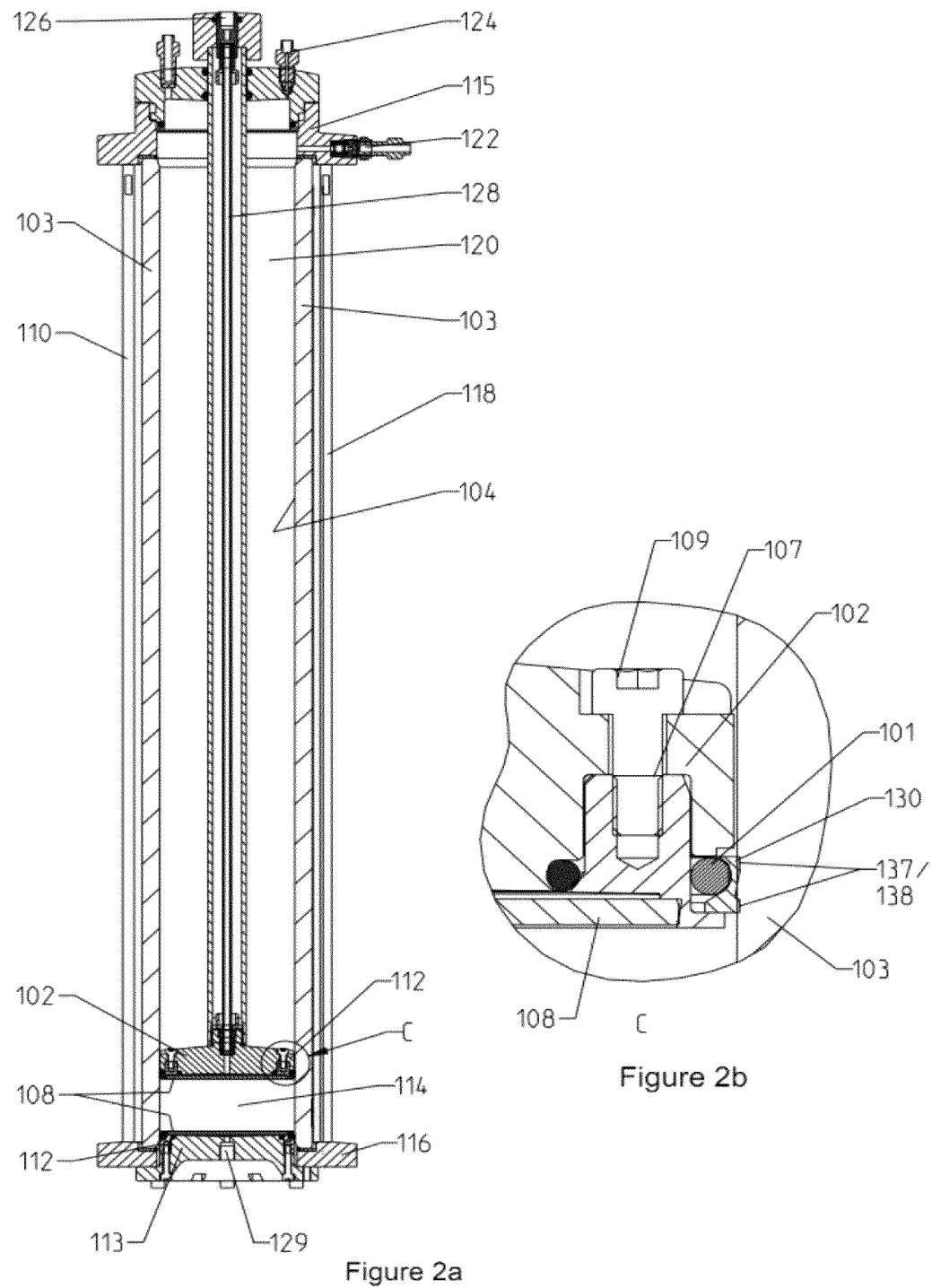
FIG. 2a and FIG. 2b are diagrams of a laboratory scale column equipped with an embodiment of a sealing assembly in accordance with the present invention. The principle features of the column are shown in FIG. 2a, while the sealing assembly is detailed in the inset C of FIG. 2b.

FIG. 2 is a cross-sectional view of a laboratory-scale chromatography column (FIG. 2a) showing the positioning and configuration of a sealing assembly of the present invention (inset C shown in FIG. 2b). The invention is described in relation to a small column but the skilled person will understand that the same principles apply for its use in a larger industrial-scale column.

Column 110 comprises a cylindrical housing 103 (or wall or tube) having an inner cylindrical surface 104 which together with nets 108 (which are affixed to retaining rings (e.g. 107) to form two bed supports 112 fastened to the adapter 102 and the bottom plate 113) delimit a media chamber or cavity 114 for a bed of chromatographic media. The housing 103 is made of glass or a suitable plastic such as an acrylate-based polymer and is supported by top 115 and bottom 116 flanges and extender rods 118. Columns having a metallic housing 103, such as stainless steel, may also be used (particularly for larger columns such as industrial scale columns). The bed of chromatographic media is packed by the movable adapter 102 which is driven by means of a hydraulic chamber 120. Valves 122 and 124 control liquid/media and air input/exit from the column. Buffer or liquids containing samples to be chromatographed are added to the column at port 126, flow through tubing 128 and enter the media chamber 114 where they are subjected to chromatographic separation and exit the column at collection port 129. The skilled person will also understand that it is possible to effect chromatographic separation in the opposite direction, samples being added at port 129 into chamber 114 where separation occurs, samples then flowing through the tubing 128 to be collected at port 126.

The configuration of a sealing assembly of the present invention can be seen in detail in inset C (FIG. 2b). The assembly comprises an O-ring 101 which is located adjacent the adapter backing plate 102, bed retaining ring 107 (which is affixed to net 108) and sealing element 130. A fastener 109 secures the adapter backing plate 102 to the bed retaining ring 107 and net 108. When the O-ring 101 is compressed it exerts a force against the compressive face of sealing element 130 thereby pushing the sealing face (edges 137/138) of the element 130 against the interior surface 104 of cylindrical housing 103 to form a seal.

Sealing elements similar to those of the invention are available from Repack-S, ZI du Bois Bernoux—F71290 CUISERY France see website for Repack-S. Embodiments of the seals of the present invention differ from those commercially available from Repack-S in several respects; thus, for example, leading edge 137 has been made very smooth to enhance sealing with the interior surface of the housing, while edge 137' has been sharpened to improve its media scraping properties and avoid media leakage.

Figure 3A:
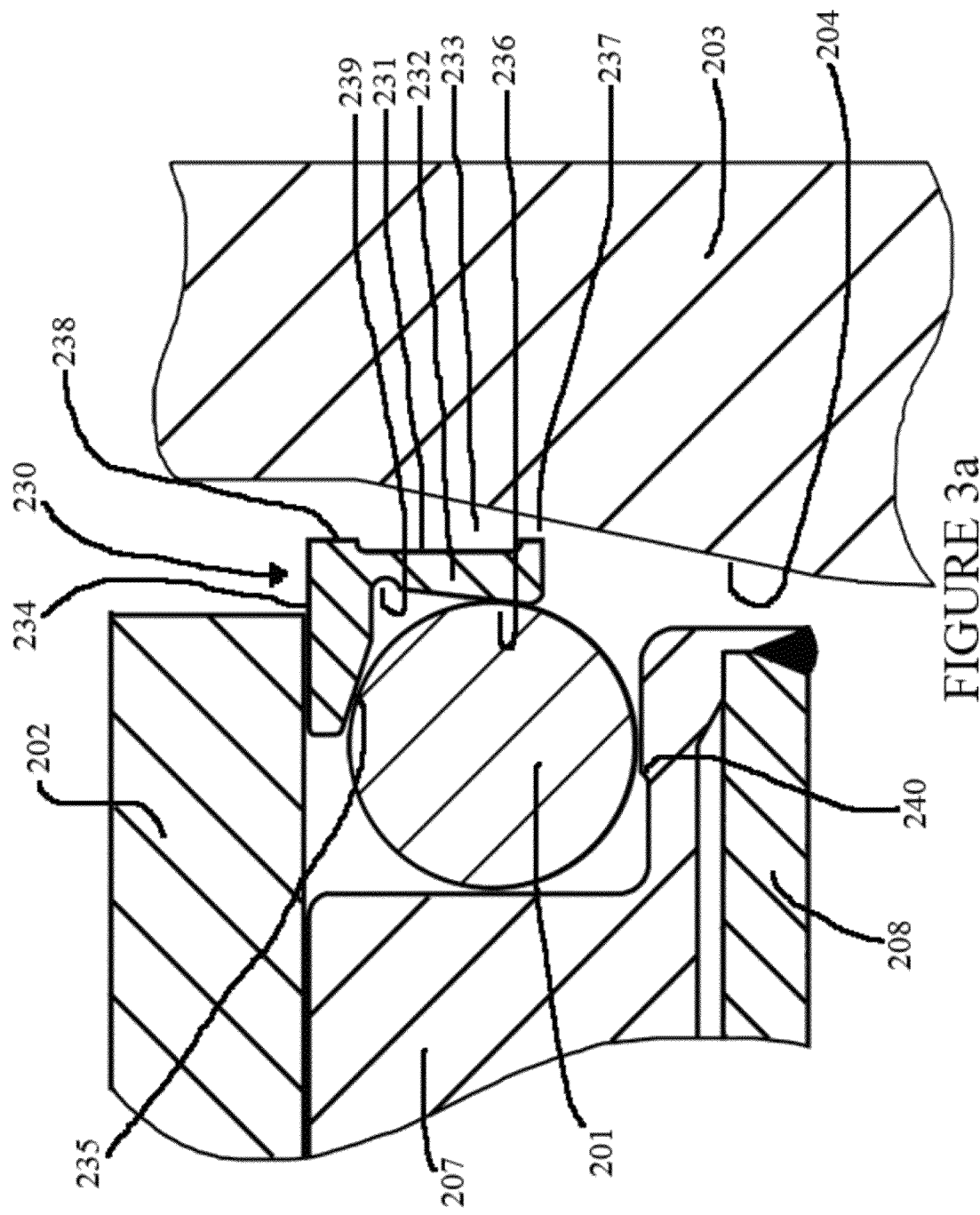
FIG. 3a and FIG. 3b depict a different embodiment of the present invention which is typically used in industrial scale chromatography columns. The sealing assembly is shown in the resting and active (compressed) states in FIG. 3a and FIG. 3b, respectively.
Figure 3B:
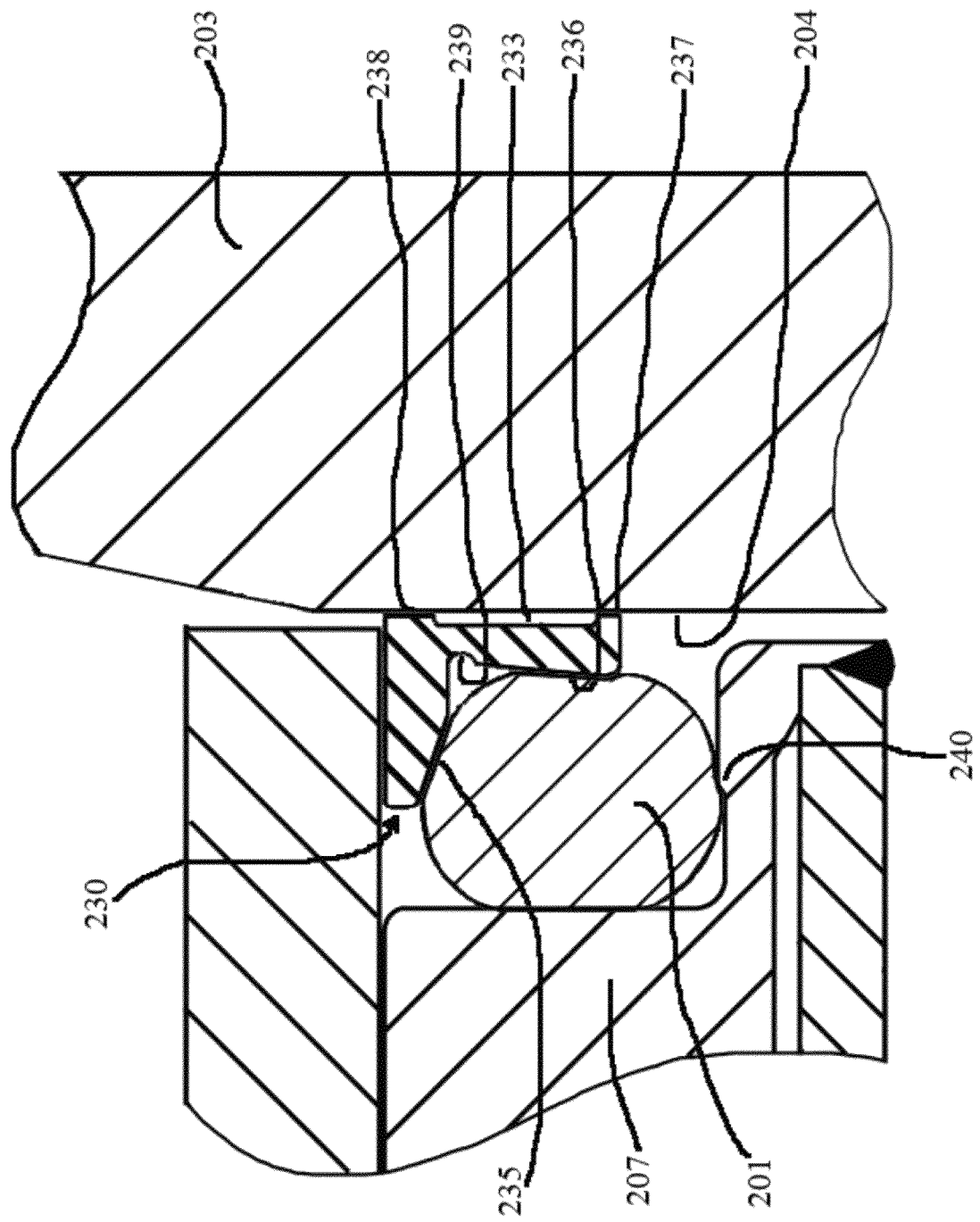

Another embodiment of the sealing assembly of the present invention is shown in FIGS. 3a and 3b. In FIG. 3a the assembly is shown in its resting position while in FIG. 3b it is in its active position with the sealing surface against the internal of the wall.

The sealing assembly consists of O-ring 201 and sealing element 230 and is located in a recess between the adapter distributor 202, the internal wall 204 of the housing 203 and the bed retaining ring of the adapter 207 (seen here welded to the net 208). In FIG. 3a the sealing assembly is in its relaxed state, as the sealing element 230 is not in contact with the internal wall 204 of the column. The O-ring 201 is made of a resilient material such as a fluorinated elastomer (e.g. FKM) or EPDM rubber and the sealing element is composed of a material having a low coefficient of friction and which is extremely durable such as UHMWPE (Ultra High Molecular Weight Poly Ethylene). Durability is important in order to avoid abrasion of the column and wearing of the element.

The sealing element 230 is L-shaped and consists of two legs or arms 232/234, each leg having a compressive surface 235/236 adjacent the O-ring 201, one leg 232 having an opposed sealing surface 233 bearing a raised leading edge 237 and a raised trailing edge 238. Seals are formed between the O-ring 201 and the sealing element 230 at compressive surfaces 235 and 236, and also between the O-ring 201 and the bed retaining ring 207 adjacent to the chamfer 240. The area of the sealing surface 233 between the raised leading and trailing edges 237/238 is recessed 231 to allow the sealing surface to flex and cope with tolerances. The intersection of the legs 232/234 is indented 239 while the compressive face on each leg is angled relative to the indent. The purpose of the indent 239 and the angled face on each compressive surface 235/236 is to concentrate and/or maximise the force exerted by the resilient member 201 on the raised leading 237 and trailing 238 edges on the cylindrical surface 204 and thus provide a strong seal. In its resting position, the O-ring 201 pushes the leg 234 of the sealing element 230 against the distributor 202 thereby locking it into position. This makes it possible to fill the column by negative pressure (e.g. aspirating media from the bottom of the column) of around −0.5 bar. The seal is designed to operate between approximately −0.8 bar to a pressure of approximately +20.0 bar and at temperatures of +2° C. to +36° C. Preferably the seal is used in columns operated at pressures of between −0.5 bar to +5.7 bar and at temperatures of +4° C. to +30° C.

As the adapter moves down the column, the sealing element 230 makes contact with the cylindrical wall 204 of the column (FIG. 3b). This results in compression of the O-ring 201 which being resilient in nature exerts a force against the compressive surfaces 235/236 of the sealing element 230. The surfaces 235/236 and the indent 239 of the sealing element 230 are designed such that the exerted force is concentrated on the raised leading 237 and trailing 238 edge, thereby forming a tight seal with the cylindrical surface 204 of the column housing 203. A chamfer 240 on the lower face of the bed retaining ring of the adapter 207 enhances the seal between the O-ring 201 and the retaining ring 207.

Figure 4:
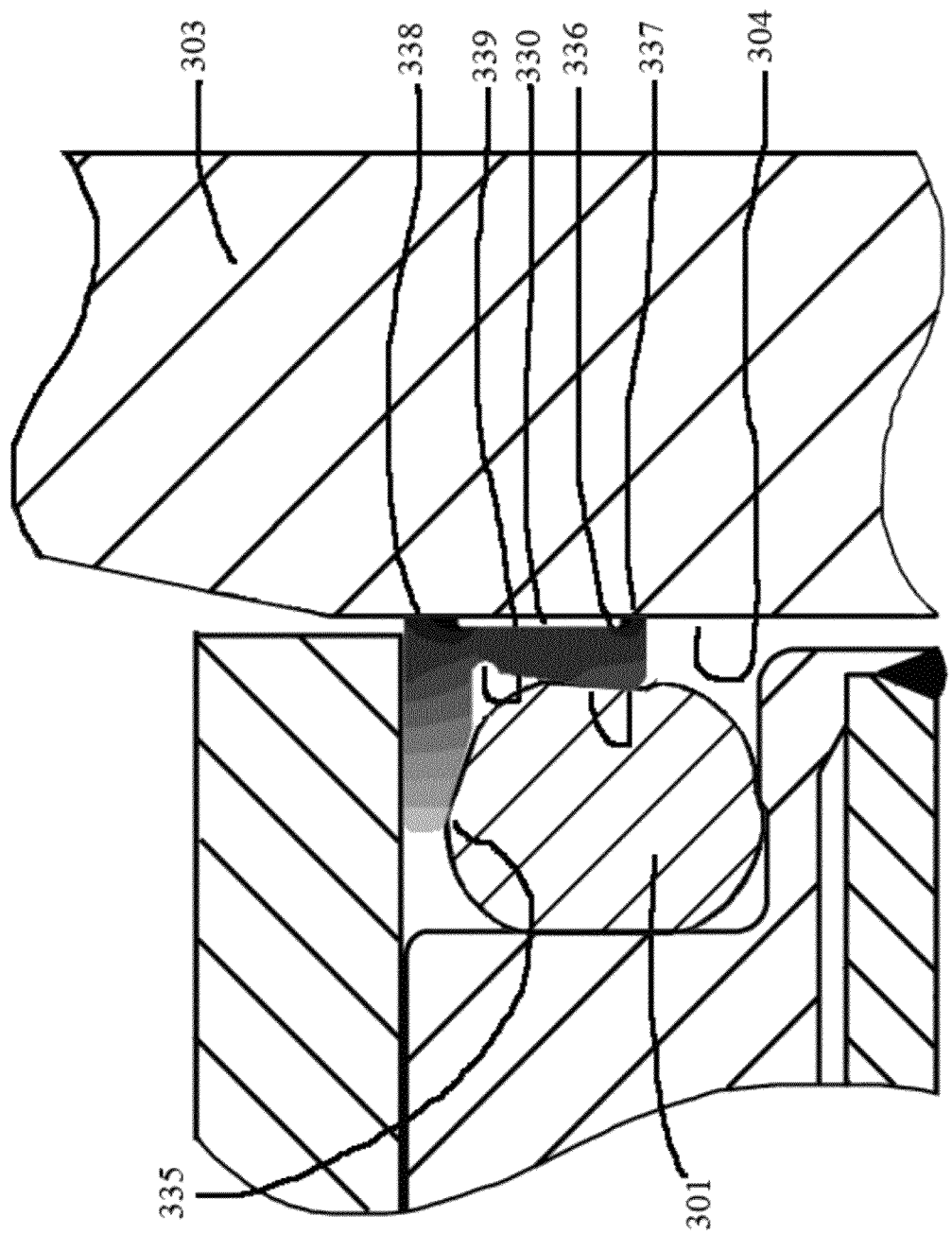
FIG. 4 is a stress diagram illustrating the regions of low to high stress in the sealing element of the sealing assembly of FIG. 3 when it is in an active (compressed) state.

FIG. 4 shows a stress diagram illustrating the regions of low to high stress in the sealing element 330 of the sealing assembly of FIG. 3b (i.e. when it is in an active or compressed state). The regions of stress were determined using an ANSYS analysis program (see website for Ansys, Inc.). Maximum stress (seen as areas of darkest coloration in the Figure) occurs at the raised leading 337 and trailing 338 edge of the sealing surface 333, thereby forming a tight seal with the cylindrical surface of 304 of the housing 303. The sealing element 330 has been designed to focus the force exerted by the O-ring 301 on edges 337/338 by means of indent 339 and angling the compressive surfaces 335/336 relative to the indent 339.

Microbiological growth within chromatography columns can lead to problems in terms of chromatographic performance and contamination, in extreme cases leading to the loss of high value analytes. Poor seals allow "pocket" formation which open and close during the operation of the column, opening to allow microbes to enter behind the seal and grow but then closing to prevent chemical sterilants, used to sanitise the column, from reaching and killing the microbes. Tests were therefore conducted to determine whether or not the sealing assembly of the invention entrap bacteria which can then proliferate and avoid sanitization with sterilants. No colony-forming microbes were found at any sampling location in any of the two tests conducted. The sealing assembly of the invention therefore allow sanitisation by sterilants such as sodium hydroxide and other suitable antimicrobial agents and chemicals.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A sealing assembly for a chromatography column for sealing between an adapter and an inner cylindrical surface of a cylindrical housing, said assembly comprising a sealing element composed of a material having a low coefficient of friction and a separate resilient member co-operating therewith, said sealing element comprising a first and a second leg wherein, said first leg comprises opposed first and second faces, said first face being a sealing surface comprising a raised leading and a raised trailing edge, said second face comprising a compressive surface, and said second leg comprising a compressive surface;
wherein said resilient member exerts a force against said compressive surfaces of the sealing element to form a seal between said raised leading and trailing edges and said cylindrical surface.

2. The sealing assembly of claim 1, wherein said assembly is movable along the axial axis of the cylindrical surface.

3. The sealing assembly of claim 1, wherein the sealing element is L-shaped.

4. The sealing assembly of claim 1, wherein the compressive surfaces of the first and second legs of the sealing element are indented at there intersection to maximise and/or concentrate the force exerted on the raised leading and trailing edges on the cylindrical surface.

5. The sealing assembly of claim 1, wherein the compressive surfaces of the first and second legs of the sealing element are angled relative to said indent to maximise and/or concentrate the force exerted by the resilient member on the raised leading and trailing edges on the cylindrical surface.

6. The sealing assembly of claim 1, wherein the sealing element is composed of ultra high molecular weight polyethylene.

7. The sealing assembly of claim 1, wherein the resilient member is an O-ring.

8. The sealing assembly of claim 1, wherein the resilient member is an O-ring composed of a fluoroelastomer or an EPDM rubber.

9. The sealing assembly of claim 1, wherein the strength of the seal formed between the raised leading and trailing edges and the cylindrical surface is independent of the pressure applied to the adapter.

10. The sealing assembly of claim 1, wherein the seal so formed is stable across a temperature range of +2° C. to +36° C.

11. The sealing assembly of claim 1, wherein the seal so formed is stable across a pressure range of −0.8 bar to +20.0 bar.

12. A chromatography column comprising a cylindrical housing having an inner cylindrical surface, an adapter within said housing, and a sealing assembly of claim 1 for forming a seal between said adapter and said inner cylindrical surface.

13. A method of sanitising a chromatography column, said method comprising treating said column comprising the sealing assembly of claim 1 with a sanitising agent and then neutralising said agent.

* * * * *